United States Patent [19]
Tidwell et al.

[11] Patent Number: 5,578,631
[45] Date of Patent: Nov. 26, 1996

[54] METHODS OF COMBATING PNEUMOCYSTIS CARINII PNEUMONIA AND COMPOUNDS USEFUL THEREFOR

[75] Inventors: Richard R. Tidwell; Christine C. Dykstra; James E. Hall, all of Chapel Hill, N.C.

[73] Assignee: The University of North Carolina at Chapel Hill, Chapel Hill, N.C.

[21] Appl. No.: 427,597

[22] Filed: Apr. 24, 1995

Related U.S. Application Data

[62] Division of Ser. No. 958,696, Oct. 13, 1992, Pat. No. 5,428,051.

[51] Int. Cl.[6] ............... A61K 31/415; A61K 31/55; A61K 31/505; C07D 403/14
[52] U.S. Cl. ............... 514/394; 548/306.1; 544/296; 544/333; 540/553; 514/256; 514/218
[58] Field of Search ............... 548/306.1; 514/394, 514/256, 218; 544/296, 33 B; 540/553

[56] References Cited

U.S. PATENT DOCUMENTS

| | | | |
|---|---|---|---|
| 4,933,347 | 6/1990 | Tidwell et al. | 514/256 |
| 4,963,589 | 10/1990 | Tidwell et al. | 514/636 |
| 5,428,051 | 6/1995 | Tidwell et al. | 514/394 |

OTHER PUBLICATIONS

Dubovi et al., Antimicrob. Ag. Chemoth., 19(4), 649–56 (1981).
Geraty, et al. Am. J. Path., 139(4), 921–31 (1991).
Tidwell et al. J. Med. Chem. 21, 613–23 (1978).
J. Anne, et al; Antifungal and Antibacterial Activities of Diarylamidine Derivatives, *Antimicrobial Agents and Chemotherapy* pp. 231–239 (Aug. 1980).
C. Bell et al.; Structure–Activity Relationships of Pentamidine Analogs against Giardia lamblia and Correlation of Antigiardial Activity with DNA–Binding Affinity; *Antimicrobial Agents and Chemotherapy* 35 No. 6, 1099–1107 (1991).
M. Cory et al.; Structure and DNA Binding Activity of Analogues of 1,5–Bis(4–amidinophenoxy) pentane (Pentamidine); *Journal of Medicinal Chemistry* 35 No. 3, 431–438 (1992).
C. Dykstra and R. Tidwell, Inhibition of Topoisomerases from *Pneumocystis carinii* by Aromatic Dicationic Molecules; *J. Protozool* 38 No. 6, 78S–81S (1991).
S. Jones et al.; Novel Pentamidine Analogs in the Treatment of Experimental *Pneumocystis carinii* Pneumonia; *Antimicrobial Agents and Chemotherapy* 34 No. 6, 1026–1030 (1990).
R. Tidwell et al.; Treatment of Experimental *Pneumocystis carinii* Pneumonia with 1,3–Di(4–Imidazolino–2–Methoxyphenoxy)Propane Lactate; *J. Protozool*, 38 No. 6, 148S–150S (1991).
R. Tidwell et al.; Development of Pentamidine Analogues as New Agents for the Treatment of *Pneumocystis carinii* Pneumonia[a]; *Annals of the New York Academy of Sciences* 616:421–441 (1990).
R. Tidwell et al,; Analogues of 1,5–Bis(4–amidinophenoxy)pentane (Pentamidine) in the Treatment of Experimental *Pneumocystis carinii* Pneumonia; *Journal of Medicinal Chemistry* 33:1252–1257 (1990).
R. Tidwell et al.; Diarylamidine Derivatives with One or Both of the Aryl Moieties Consisting of an Indole or Indole–like Ring. Inhibitors of Arginine–Specific Esteroproteases: *Journal of Medicinal Chemistry* 21:613–623 (1978).

*Primary Examiner*—Johann Richter
*Assistant Examiner*—Laura R. Cross
*Attorney, Agent, or Firm*—Bell, Seltzer, Park & Gibson

[57] ABSTRACT

Disclosed is a method of combating *Pneumocystis carinii* Pneumonia in a subject in need of such treatment. The method comprises administering to to the subject an effective *Pneumocystis carinii*-combating amount of a bis-benzimidazole compound such as bis[5-(2-imidazolyl)-2-benzimidazolyl]methane, 1,4-bis[5-2-imidazolyl)-2-benzimidazolyl]butane, or a pharmaceutically acceptable salt thereof. Pharmaceutical formulations for carrying out the method and novel compounds are also disclosed, along with methods of combating *Giardia lamblia*.

3 Claims, No Drawings

METHODS OF COMBATING *PNEUMOCYSTIS CARINII* PNEUMONIA AND COMPOUNDS USEFUL THEREFOR

The present invention was made with Government support under Grant Number NO1-AI 72648 from the National Institutes of Health. The Government has certain rights to this invention.

This application is a divisional of prior application Ser. No. 07/958,696, filed 13 Oct., 1992, now U.S. Pat. No. 5,428,091; the disclosure of which is incorporated by reference herein in its entirety.

FIELD OF THE INVENTION

The present invention relates to methods of combatting *Pneumocystis carinii* Pneumonia with bis-benzimidazoles, and novel bis-benzimidazoles useful therefore.

BACKGROUND OF THE INVENTION

Pentamidine, in the form of its hydrochloride salt, was first discovered by Ewins et al., as shown in U.S. Pat. No. 2,277,861, and water-soluble salts were subsequently developed as shown by U.S. Pat. No. 2,410,796 to Newberry et al, which is directed to such water soluble salts, particularly the hydroxy-ethane sulfonic acid and the hydroxy-propane sulfonic acid salts of pentamidine. the former compound is generally referred to as pentamidine isethionate.

Pentamidine isethionate is presently marketed by LyphoMed, Inc. under the trademark Pentam, for intravenous and intramuscular injection, and is indicated for the treatment of pneumonia due to *Pneumocystis carinii*, the latter ailment typically being referred as "PCP". The importance of pentamidine isethionate has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine isethionate has found utility not only in the treatment of PCP, but also of prophylaxis, in preventing or delaying the initial onset or recurrence of PCP, especially in AIDS patients.

However, an unfortunate side effect of pentamidine isethionate is its toxicity. Some fatalities have been attributed to severe hypotension, hypoglycemia, and cardiac arrhythmias in patients treated with pentamidine isethionate, through both intramuscular and intravenous routes. Because of the concern over the toxicity of pentamidine isethionate, a severe need has arisen for a replacement for pentamidine isethionate which can avoid or minimize the undesirable side effects associated with the use of pentamidine.

SUMMARY OF THE INVENTION

A first aspect of the present invention is a method of combating *Pneumocystis carinii* Pneumonia in a subject in need of such treatment. The method comprises administering to the subject an effective *Pneumocystis carinii*-combating amount of a compound according to Formula (I):

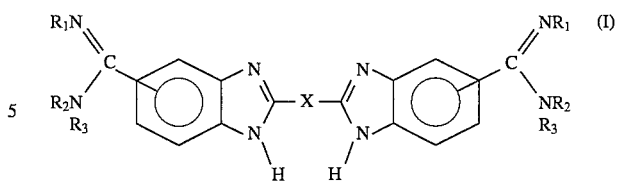

wherein:

$R_1$ and $R_2$ are each independently selected from the group consisting of H or loweralkyl, or $R_1$ and $R_2$ together represent —$(CH_2)_m$— wherein m is from two to four;

$R_3$ is H or loweralkyl; and

X is C1 to C12 linear or branched, saturated or unsaturated alkyl containing up to four double bonds (e.g., —$(CH_2)_n$— wherein n is from 1–8, which is unsubstituted or substituted from 1 to 2 times with loweralkyl, and which is saturated or unsaturated and contains up to two double bonds);

or a pharmaceutically acceptable salt thereof. Currently preferred are bis[5-(2-imidazolyl-2-benzimidazolyl]methane and 1,4-bis[5-(2-imidazolyl)-2-benzimidazolyl]butane, or pharmaceutically acceptable salts thereof.

A second aspect of the present invention is a method of combating combating *Giardia lamblia* in a subject in need of such treatment. The method comprises administering to the subject an effective *Giardia lamblia*-combating amount of a compound according to Formula (I) as given above, or a pharmaceutically acceptable salt thereof. Currently preferred is trans-1,2-bis(5-amidino-2benzimidiazolyl)ethene, or the pharmaceutically acceptable salts thereof.

A third aspect of the present invention is a compound according to formula (I) above, wherein:

$R_1$ and $R_2$ together represent —$(CH_2)_m$— wherein m is from two to four;

$R_3$ is H or loweralkyl; and

X is selected from the group consisting of —$CH_2$—$CH_2$—$CH_2$—$CH_2$—, —CH=CH—$CH_2$—$CH_2$—,

—$CH_2$—CH=CH—$CH_2$—, —CH=CH—CH=CH—, and any of the foregoing substituted from 1 to 2 times with loweralkyl;

and the pharmaceutically acceptable salts thereof. Such compounds may be included in a therapeutically effective amount in a pharmaceutically acceptable carrier to provide novel pharmaceutical formulations, with the therapeutically effective amount being effective to carry out any of the methods set forth above.

A fourth aspect of the present invention is the use of compounds of Formula (I) above for the preparation of a medicament for combating *Pneumocystis carinii* Pneumonia.

A fifth aspect of the present invention is the use of compounds of Formula (I) above for the preparation of a medicament for combatting *Giardia lamblia*.

The foregoing and other objects and aspects of the present invention are explained in detail in the specification set forth hereinbelow.

DETAILED DESCRIPTION OF THE INVENTION

The term "loweralkyl," as used herein, refers to C1 to C4 linear or branched alkyl, such as methyl, ethyl, propyl, butyl, isopropyl, sec-butyl, and tert-butyl. Methyl and ethyl are preferred.

Subjects to be treated by the methods of the present invention are typically human subjects.

As noted above, the present invention provides pharmaceutical formulations comprising the aforementioned compounds of Formula I, or pharmaceutically acceptable salts thereof, in pharmaceutically acceptable carriers for aerosol, oral, and parenteral administration as discussed in greater detail below. Also, the present invention provides such new compounds or salts thereof which have been lyophilized and which may be reconstituted to form pharmaceutically acceptable formulations for administration, as by intravenous or intramuscular injection.

Obviously, the therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 20 mg/kg will have therapeutic efficacy, with still higher dosages potentially being employed for oral and/or aerosol administration. Toxicity concerns at the higher level may restrict intraveneous dosages to a lower level such as up to about 10 mg/kg, all weights being calculated based upon the weight of the active base, including the cases where a salt is employed. Typically a dosage from about 0.56 mg/kg to about 5 mg/kg will be employed. The duration of the treatment is usually once per day for a period of two to three weeks or until the *Pneumocystis carinii* pneumonia is essentially controlled. Lower doses given less frequently can be used to prevent or reduce the incidence of recurrence of the infection.

In accordance with the present method, a compound of Formula I, or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the also provides a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As *Pneumocistis carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula I or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immunocompromised patient who has never experienced an episode of *Pneumocystis carinii* pneumonia. In this respect, a patient who has ben diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula I or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filing should be done by an aseptic method. Sterilized closures may then be placed on the vials and, if desired, the vial contents may be lyophilized.

In addition to compounds of Formula I or their salts, the pharmaceutical compositions may contain other additives, such pH adjusting additives. In particular, useful pH adjusting agents include acids or bases or buffers, such a sodium lactate, sodium acetate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well know in the art.

In yet another aspect of the present invention, there is provide an injectable, table, sterile composition comprising a compound of Formula I, or a salt thereof, in a unit dosage form in a sealed container. The compound or salt is provided in the form of a lyopholizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous based emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well know in the art. When the compound of Formula I or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as though the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds exemplary of Formula (I) above include, but are not limited to:

(1) bis[5-amidino-2-benzimidazolyl]methane;

(2) bis[5-(2-imidazolyl)-2-benzimidazolyl]methane;

(3) 1,2-bis[5-amidino-2-benzimidazolyl]ethane;

(4) 1,2-bis[5-(2-imidazolyl)-2-benzimidazolyl]ethane;

(5) 1,3-bis[5-amidino-2-benzimidazolyl]propane;

(6) 1,3-bis[5-(2-imidazolyl)-2-benzimidazolyl]propane;

(7) 1,4-bis[5-amidino-2-benzimidazolyl]propane;

(8) 1,4-bis[5-(2-imidazolyl)-2-benzimidazolyl]butane;

(9) 1,8-bis[5-amidino-2-benzimidazolyl]octane;

(10) trans-1,2-bis[5-amidino-2-benzimidazolyl]ethene;

(11) 1,4-bis[5-(2-imidazolyl)-2-benzimidazolyl]1-butene;

(12) 1,4-bis[5-(2-imidazolyl)-2-benzimidazolyl]2-butene;

(13) 1,4-bis[5-(2-imidazolyl)-2-benzimidazolyl]1-methylbutane;

(14) 1,4-bis[5-(2-imidazolyl)-2-benzimidazolyl]2-ethylbutane;

(15) 1,4-bis[5-(2-imidazolyl)-2-benzimidazolyl]1-methyl-1-butene;

(16) 1,4-bis[5-(2-imidazolyl)-2-benzimidazolyl]2,3-diethyl-2-butene;

(17) 1,4-bis[5-(2-imidazolyl)-2-benzimidazolyl]1,3-butadiene; and

(18) 1,4-bis[5-(2-imidazolyl)-2-benzimidazolyl]2-methyl-1,3-butadiene.

Compounds of Formula (I) analogous to the foregoing can be produced by substituting a 2-pyrimidyl group for the 2-imidazolyl group.

Compounds employed in carrying out the present invention are either known or may be prepared in accordance with techniques known to those skilled in the art (see, e.g., U.S. Pat. No. 4,933,347), particularly in light of the disclosure set forth below.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the amidine base compound with the desired acid, in solution. After the reaction is complete, the salts are crystallized from solution by the addition of an appropriate amount of solvent in which the salt is insoluble.

Methods of combating *Giardia lamblia* with the compounds of Formula (I) as given above are carried out in essentially the same manner as given above, and pharmaceutical formulations of the compounds of Formula (I) for combating *Giardia lamblia* are prepared in essentially the same manner as given above.

The present invention will be further illustrated by the following non-limiting examples.

EXAMPLE 1

Synthesis of 1,4-Bis[5-(2-Imidazolyl)-2-Benzimidazolyl]Butane (Compound 8)

p-Cyanoaniline was acetylated with acetic anhydride to give 90% yield of the N-acetylated intermediate. The intermediate was nitrated using standard conditions to give 50% yield of 4-cyano-2-nitroaniline. Reduction of the nitro group with 10% Pd-C in Par hydrogenator afforded 2-amino-4-cyanoaniline in 85% yield. The di-imidate was formed from 1,4-dicyanobutane in ethanol and benzene, saturated with HCl. The reaction was carried out according to the procedures described in R. Tidwell et al., *J. Med. Chem.* 21:613–623 (1978) and required 24 hours for conversion of both nitrile groups to the imidate moieties.

2.56 g (9.4 mmol) of the di-imidate and 2.5 g (18.8 mmol) of the 2-amino-4-cyanoaniline were placed in acetic acid and heated to reflux for 24 h. The reaction mixture was cooled to room temperature and the acetic acid stripped off in vacuum. The residue was basified with ammonium hydroxide (pH=7.5). The solid material was collected by filtration, washed with water and dissolved in ethanol. The ethanol solution was acidified with HCl and a solid collected by filtration. The solid was washed with hot methanol to give 1.9 gr of final intermediate as a white solid (4.9% yield, MP=335° C., dec). High pressure liquid chromatography showed the purity of the product to be 97%+. The product was confirmed by NMR and elemental analysis (Theory: C=58.12, H=4.39, N=20.34; Found: C=58.20, H=4.36, N=20.34).

A suspension of the final intermediate (1.8 g 4.4 mmol) in dioxime (110 ml) and MeOH (25 ml) was chilled to 8° C. The cooled mixture was saturated with HCl gas for 1 h while maintaining the temperature at 8° C. The mixture was stopped and allowed to stir ar room temperature until the nitrile peak was no longer evident in the infrared spectra (3 days). The reaction mixture was chilled on an ice bath and the product precipitated with diethyl ether. The solid was filtered under $N_2$ and suspended in anhydrous ethanol (100 ml). Ethylenediamine (1.76 ml, 1.50 g, 26.4 mmol) was added to the suspension and the mixture heated to reflux for 2.5 h. The ethanol was removed and the residue solid was washed in diethyl ether. The solid was collected and dissolved in dilute HCl. The solution was decolorized with charcoal and $Na_2CO_3$ added until no more precipitate formed. The solid was collected and dried to give 1.5 g of the product (60% yield, MP=319°–321° dec). The product was found to be 97% pure by HPLC. The structure was confirmed by NMR and elemental analysis (Theory: C=50.36, H=5.28, N=19.58; Found: C=50.16, H=6.32N=19.39).

EXAMPLE 2

Synthesis of
Bis[5-Amidino-2-Benzimidazolyl]Methane
(Compound 2) and
1,3-Bis[5-(2-Imidazolyl)-2-Benzimidazolyl]Propane
(Compound 6)

These compounds were synthesized in essentially the same manner as that described in Example 1 above with the appropriate starting materials. Physical data are given in Table 1 below.

TABLE 1

Physical Data for Novel Benzimidazole Compounds

| Compound No. | Melting Point (°C.) | Analysis (calculated/found), % | | |
|---|---|---|---|---|
| | | C | H | N |
| 2 | 277–279 | 51.12/50.88 | 5.31/5.38 | 22.71/22.64 |
| 6 | 242–245 | 47.93/47.89 | 5.25/5.32 | 19.44/19.37 |

EXAMPLE 3

Induction and Treatment of *Pneumocystis carinii* in Sprague-Dawley Rats

Male Sprague-Dawley rats, barrier raised, non-certified virus free, weighing 150–200 g were obtained from Hilltop Laboratories and housed individually. Animals were begun on a low (8%) protein diet (ICN Biomedicals, Cincinnati, Ohio and drinking water containing tetracycline (0.5 mg/ml) and dexamethasone (1.0 μg/ml). This treatment was given for the next 8 weeks, monitoring fluid intake daily and weighing animals weekly. Dilutions of the drinking solution were made when animals consumed too much fluid so as to prevent cortisone poisoning. At the beginning of the sixth week animals were divided into groups of eight or more animals each and the test compounds were administered daily by i.v. injection into the tail vein at the indicated dose for the next 14 days or orally by gavage for the next 14 days.

All animals were sacrificed at the end of the eighth week by chloroform inhalation and the right lung was inflated in situ with 10% formalin and fixed for histologic examination. The fixed lung tissue was sectioned longitudinally and stained with Grocott's methenamine silver (GMS) stain which selectively stains the walls of th *P. carinii* cysts. Stained sections were coded and each section was scored by 2 examiners using a blinded protocol. Sections were read and scored according to modification of known procedures (P. Walzer et al., *Antimicrobo Agents. Chemother.* 32: 896–905 (1988)) as follows: 0.5=less than 10 cysts counted per two fully examined sections; 1=scattered cysts with<10% of lung tissue involved; 2=scattered cysts with limited intense focal involvement and 10 to 25% of lung tissue involved; 3=scattered cysts with numerous intense areas of focal involvement and 26 to 50% of lung tissue involved; 4=cysts found throughout the tissue with numerous very intense focal areas of involvement having>50% of lung tissue involved.

The left lung was weighed, ground through a #60 wire mesh, and suspended 1:10 (w/v) in Hank's balanced salts solution without cations (HBSS-) and 10 mM β-mercaptoethanol (β-Me). Slides were prepared by spotting 5 μl of lung homogenate diluted 1:10 in HBSS- with β-Me and allowed to air dry. The slides were stained with cresyl violet and the cysts were counted using a blinded protocol. The number of cysts/g of original lung tissue was calculated and the groups were reported as the percent of saline-treated controls.

Toxicity of the test compounds was evaluated at 10 mg/kg or the next highest soluble or non-toxic dose by the following criteria: 0=no local, clinical, or histologic toxicity; +=all animals survived the test dose without observable distress, minimal or no signs of hypotension observed, some excess weight loss was noted and/or mild signs of local toxicity at the injection site, no histopathology noted; ++=all or most animals survived the test dose with marked signs of hypotension, all animals were observed to have other clinical side effects and/or some histopathology, many animals had severe lesions at the injection site; +++=an acute toxic effect was seen after a single dose with symptoms compatible with sever hypotension and/or a sharp decrease in animals' health after multiple doses, death occured in less thant 50% of animals resulting in a reduced screening dose; ++++=death occured in greater than 50% of the animals with a resulting reduction in screening dose.

The Chi square goodness of fit was used to calculate the p values of each test group when compared to the saline-treated and pentamidine-treated groups. The statistical analysis was carried out using the StatView 512+ software package (Brainpower, Inc., Calabasas, Calif.) on a Macintosh II computer.

Data on compounds of Formula I presented in Table 2 below indicate that these are effective compounds. Compound 8 was over four times more potent as an anti-PCP agent than pentamidine and was significantly less toxic than the parent compound. Compound 8 exhibited some activity against PCP when administered orally at a daily dose of 25 mg/kg.

TABLE 2

Activity of benzimidazole compounds against *Pneumocystis carinii* pneumonia by daily i.v. injection

| Compound | Dose (mg/kg) | Mean Histologic Score (n) | No. of animals with the following histologic scores: | | | | | Toxicity[c] | Cysts/g Lung[a] (% of Control) |
|---|---|---|---|---|---|---|---|---|---|
| | | | 0.5 | 1 | 2 | 3 | 4 | | |
| Saline | — | 3.7(80) | 0 | 1 | 5 | 14 | 60 | — | 100.00 |
| Pentamidine | 10.0 | 1.3(71)[d] | 12 | 38 | 17 | 4 | 0 | 2+ | 3.13 |
| 1 | 10.0 | 0.6(8)[d] | 7 | 1 | 0 | 0 | 0 | 0 | ND |
| 2 | 5.0[e] | 0.8(8)[d] | 8 | 2 | 0 | 0 | 0 | 0 | 1.19 |
| 3 | 10.0 | 0.7(10)[d] | 7 | 3 | 0 | 0 | 0 | 2+ | 2.05 |
| 4 | 5.0 | 0.6(12)[d] | 9 | 3 | 0 | 0 | 0 | 0 | 1.54 |
| 5 | 10.0 | 3.0(12)[f] | 0 | 1 | 1 | 7 | 3 | 1+ | 64.62 |
| 6 | 10.0 | 1.4(12) | 1 | 7 | 3 | 1 | 0 | 1+ | 9.23 |
| 7 | 10.0 | 0.6(12)[d] | 10 | 2 | 0 | 0 | 0 | 0 | 1.67 |
| 8 | 10.0 | 0.5(12)[d] | 12 | 0 | 0 | 0 | 0 | 0 | 0.07 |
| 9 | 5.0 | 2.1(12) | 1 | 0 | 8 | 3 | 0 | 2+ | 31.79 |
| 10 | 5.0 | 1.5(12) | 1 | 5 | 5 | 1 | 0 | 1+ | 2.14 |

[a]Average cyst count for saline controls = $3.9 \times 10^7$;
[c]See text for explanation of toxicity;
[d]$P<.0001$ vs. saline;
[e]Tested at a reduced dose due to insufficient amount of compound;
[f]$P<.01$ vs. pentamidine.

EXAMPLE 4

In vitro Biological Activity of Bis-Benzimidazoles Against *Giardia lamblia*

*Giardia lamblia* is an important cause of diarrheal disease in the United States and throughout the world. See generally U.S. Pat. No. 4,963,589 to R. Tidwell et al. This Example was carried out to determine the activity of the instant compounds in combating *Giardia lamblia*.

These experiments were carried out in accordance with known techniques (see U.S. Pat. No. 4,963,589 to R. Tidwell et al.). In brief, *Giardia lamblia*, strain WB (ATCC #30957) was grown to early log phase in filter sterilized Keister's medium with 10% heat-inactivated fetal bovine serum and 50 µg/ml ampicillin and 50 µg/ml gentamicin sulfate. Assay medium was modified Keisterl's medium plus 5% heat-inactivated fetal bovine serum. The assay procedure was carried out in accordance with the following steps:

(1) (0 hours) Serial dilutions of diamidines suspended in assay medium were prepared in duplicate rows of a 96-well microtiter plate and $2.5 \times 10_4$ trophozoites were added to each well. Plates were placed in an anaerobic chamber, gassed with nitrogen, and incubated at 37° C.

(2) (24 hours) Added [methyl-$^3$H]-thmidine (1–10 Ci/mmol) to yield 1.5–2 µCi/well.

(3) (42 hours) Harvested cells with multimash-type cell harvester onto glass microfiber paper. Washed and dried filters were counted using a scintillation counter to determine the incorporation of [$^3$H]-thymidine.

(4) Data on uptake of [$^3$H]-thymidine were fitted to a logistic-logarithmic concentration response function by a non-linear regression method and drug concentrations required to inhibit 50% incorporation of [$^3$H]-thymidine were determined.

Data are set forth in Table 3 below. These data show that this series of compounds is effective in combating *Giardia lamblia*.

TABLE 3

In vitro Biological Activities of Bis-benzimidazoles

| Compound No. | $IC_{50} \pm$ S.D. (µM) In Vitro Antigiaridal Activity |
|---|---|
| 1 | 307 ± 28.3 |
| 2 | 105 ± 17 |
| 3 | 0.33 ± 0.15 |
| 4 | 0.21 ± 0.03 |
| 5 | 32.5 ± 6.4 |
| 6 | 49.5 ± 7.8 |
| 7 | 8.15 ± 6.9 |
| 8 | 14.5 ± 3.5 |
| 9 | 0.04 ± 0.01 |

The foregoing examples are illustrative of the present invention, and are not to be construed as limiting thereof. The invention is defined by the following claims, with equivalents of the claims to be included therein.

That which is claimed is:

1. A compound according to formula (I)

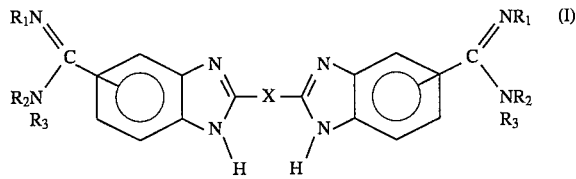

wherein:

$R_1$ and $R_2$ together represent —$(CH_2)_m$— wherein m is from two to four;

$R_3$ is H or loweralkyl; and

X is selected from the group consisting of —CH=CH—CH$_2$—CH$_2$—, CH$_2$—CH=CH—CH$_2$—, —CH=CH—CH=CH—, and any of the foregoing substituted from 1 to 2 times with loweralkyl;

and the pharmaceutically acceptable salts thereof.

2. A compound according to claim 1, which compound is selected from the group consisting of:

1,4-bis[5-(2-imidazolyl)-2-benzimidazolyl] 1-butene;
1,4-bis[5-(2-imidazolyl)-2-benzimidazolyl] 2-butene;
1,4-bis[5-(2-imidazolyl)-2-benzimidazolyl] 1-methyl-1-butene;
1,4-bis[5-(2-imidazolyl)-2-benzimidazolyl] 2,3-diethyl-2-butene;
1,4-bis[5-(2-imidazolyl)-2-mbenzimidazolyl] 1,3-butadiene;
1,4-bis[5-(2-imidazolyl)-2abenzimidazolyl] 2-methyl-1,3-butadiene;

and the pharmaceutically acceptable salts thereof.

3. A pharmaceutical composition comprising a therapeutically effective amount of a compound according to claim 1 or 2 in a pharmaceutically acceptable carrier.

* * * * *

UNITED STATES PATENT AND TRADEMARK OFFICE
CERTIFICATE OF CORRECTION

PATENT NO. : 5,578,631
DATED : November 26, 1996
INVENTOR(S) : Tidwell et al.

It is certified that error appears in the above-indentified patent and that said Letters Patent is hereby corrected as shown below:

Col. 1, Line 34, after "Pentam" insert --™--.

Col. 2, line 25, delete "combating", second instance.

Col. 2, line 30, after "amidino-2" insert -- - --.

Col. 4, line 39, replace "know" with --known--.

Col. 4, line 66, replace "know" with --known--.

Col. 9, line 45, replace "Keisterl's" with --Keister's--.

Col. 9, line 50, replace "10$_4$" with --10$^4$--.

Col. 11, line 7, replace "mbenzinidazolyl" with --benzimidazolyl--.

Col. 12, line 1, replace "2abenzimidazolyl" with --2-benzimidazolyl--.

Signed and Sealed this

Tenth Day of June, 1997

Attest:

BRUCE LEHMAN

Attesting Officer

Commissioner of Patents and Trademarks